United States Patent
Beane et al.

[19]

[11] Patent Number: 5,885,496
[45] Date of Patent: Mar. 23, 1999

[54] PRESSURIZED FEEDSHOE APPARATUS AND METHOD FOR PRECOMPACTING POWDERED MATERIALS

[75] Inventors: Glenn L. Beane, Hanover; David S. Lashmore, Lebanon, both of N.H.

[73] Assignee: Materials Innovation, Inc., West Lebanon, N.H.

Related U.S. Application Data

[60] Provisional application No. 60/019, 945, Jun. 14, 1996.

[21] Appl. No.: 953,597

[22] Filed: Oct. 17, 1997

Related U.S. Application Data

[62] Division of Ser. No. 705,343, Aug. 29, 1996.
[51] Int. Cl.[6] .................................................. B29C 43/14
[52] U.S. Cl. ........................... 264/101; 264/113; 264/120
[58] Field of Search .................................... 264/120, 112, 264/517, 101, 113

[56] References Cited

U.S. PATENT DOCUMENTS

| | | |
|---|---|---|
| 2,303,288 | 11/1942 | Lester . |
| 2,402,367 | 6/1946 | Centrall et al. ............................ 425/62 |
| 2,598,016 | 5/1952 | Richardson . |
| 2,675,584 | 4/1954 | Feinberg et al. ......................... 425/260 |
| 2,800,684 | 7/1957 | Luthman . |
| 2,967,613 | 1/1961 | Ellis et al. . |
| 3,020,589 | 2/1962 | Maritano . |
| 3,154,812 | 11/1964 | Haller . |
| 3,183,570 | 5/1965 | Vogt ........................................ 425/260 |
| 3,191,232 | 6/1965 | Haller . |
| 3,574,892 | 4/1971 | Smith . |
| 3,605,825 | 9/1971 | Hermes ................................... 425/260 |
| 3,647,333 | 3/1972 | Smith . |
| 3,690,805 | 9/1972 | Kopicko . |
| 3,697,208 | 10/1972 | Munk et al. . |
| 3,752,622 | 8/1973 | Viadana . |
| 3,764,244 | 10/1973 | Hurley et al. . |
| 3,773,446 | 11/1973 | Borrini . |
| 3,788,787 | 1/1974 | Silbereisen et al. ..................... 425/260 |
| 3,972,449 | 8/1976 | Smith . |
| 3,995,979 | 12/1976 | Fedrigo . |
| 4,036,575 | 7/1977 | Prince ...................................... 425/260 |
| 4,080,128 | 3/1978 | Schreiner et al. . |
| 4,201,530 | 5/1980 | Vogt ........................................ 425/260 |
| 4,260,346 | 4/1981 | Anderson . |
| 4,327,996 | 5/1982 | Affolder . |
| 4,352,648 | 10/1982 | Hilton . |
| 4,359,175 | 11/1982 | Lizenby . |
| 4,377,376 | 3/1983 | DeSantis . |
| 4,401,614 | 8/1983 | DeSantis . |
| 4,488,837 | 12/1984 | Mizokawa et al. . |
| 4,591,326 | 5/1986 | Adelmann . |
| 4,788,023 | 11/1988 | Buhler et al. ............................ 264/517 |
| 4,813,818 | 3/1989 | Sanzone . |
| 4,818,201 | 4/1989 | Howard . |
| 4,853,180 | 8/1989 | Howard . |
| 5,037,287 | 8/1991 | Hirai . |
| 5,071,289 | 12/1991 | Spivak . |
| 5,074,774 | 12/1991 | Nose et al. . |
| 5,184,754 | 2/1993 | Hansen . |
| 5,222,529 | 6/1993 | Zoltan . |
| 5,236,021 | 8/1993 | Bewlay et al. . |
| 5,253,993 | 10/1993 | Birkenstock et al. . |
| 5,256,053 | 10/1993 | Haguchi . |
| 5,269,463 | 12/1993 | Burks . |
| 5,460,827 | 10/1995 | Sanderson et al. ..................... 264/112 |
| 5,472,661 | 12/1995 | Gay . |
| 5,629,033 | 5/1997 | Lienau . |

*Primary Examiner*—Mary Lynn Theisen
*Attorney, Agent, or Firm*—Fran S. Wasserman

[57] ABSTRACT

A pressurized feed shoe for delivering particulate materials to fill a die cavity is provided. The feed shoe includes a feed shoe body comprising a vessel for receiving a quantity of particulate material. The feed shoe body has at least one bottom egress opening for registering with the die cavity and a top ingress opening for receiving particulate material. A pressure generator for generating supra-atmospheric pressures within the vessel and the die cavity is also provided. The pressure generator communicates with the vessel via a conduit sealingly engaged thereto. A shuttle selectively moves the feed shoe body to and from a position whereby the bottom egress opening registers with the die cavity.

5 Claims, 9 Drawing Sheets

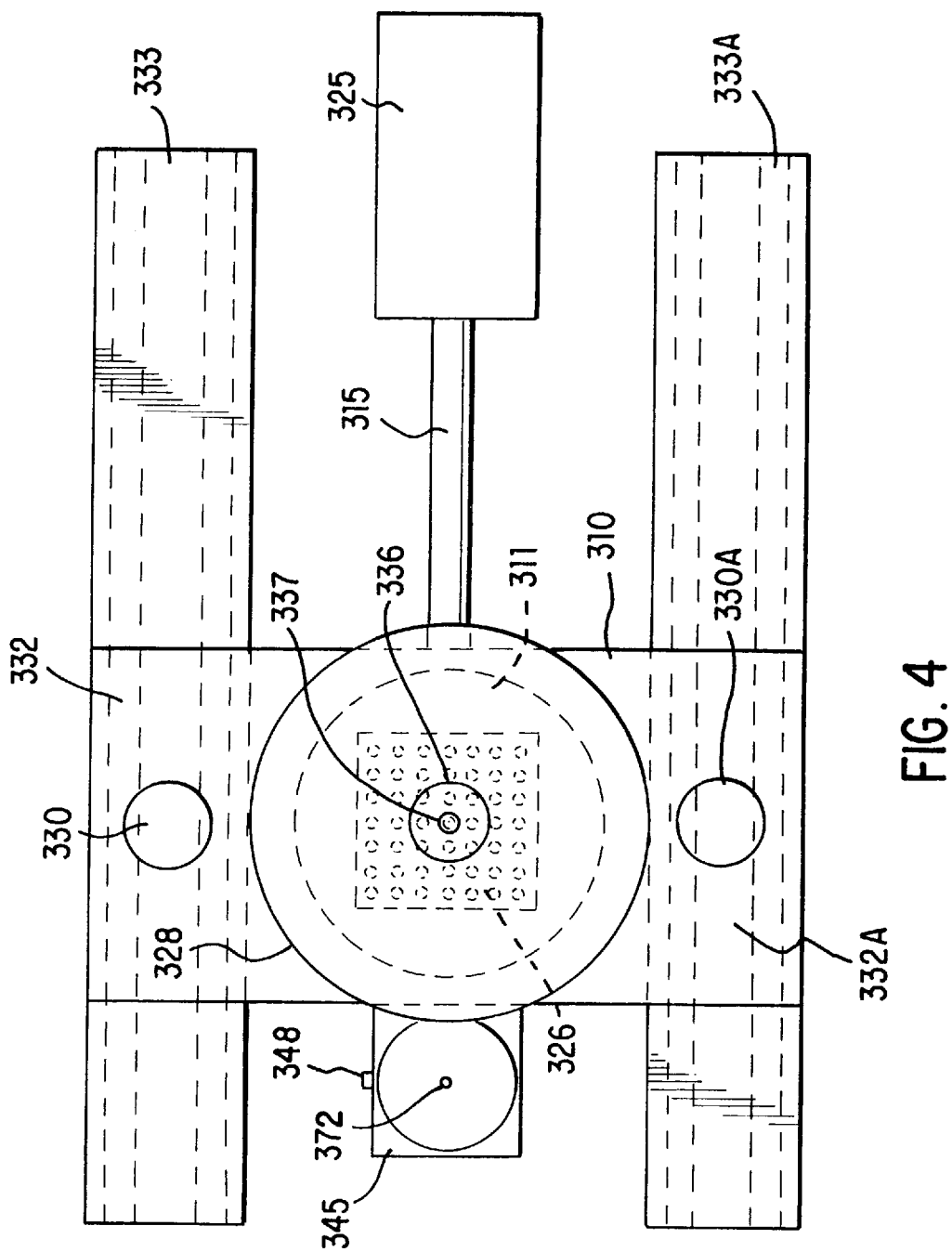

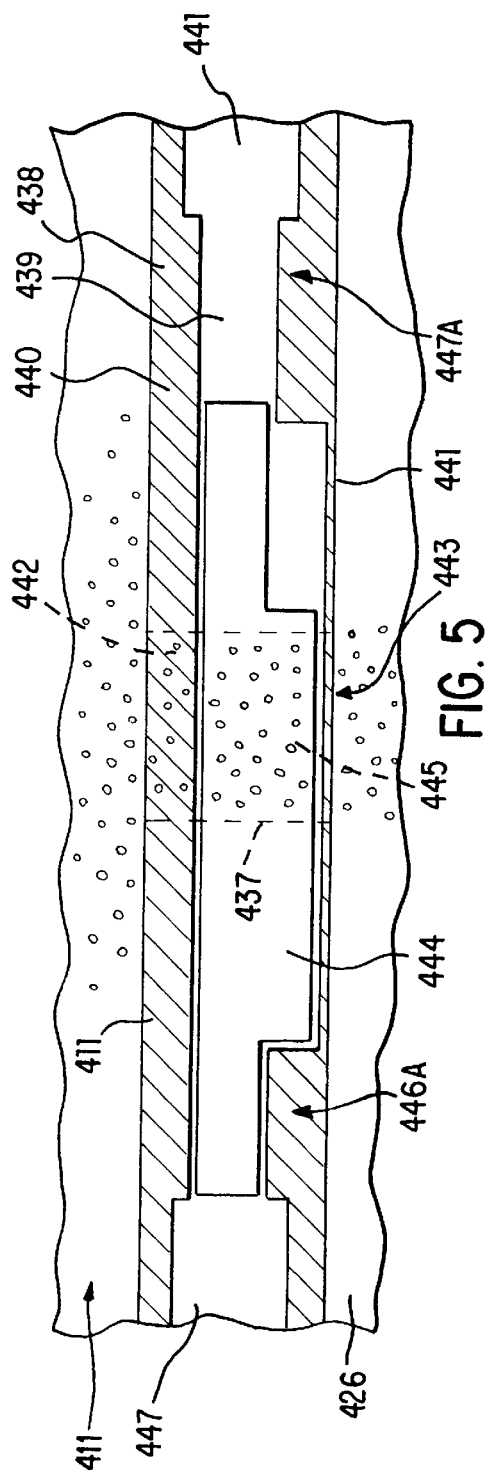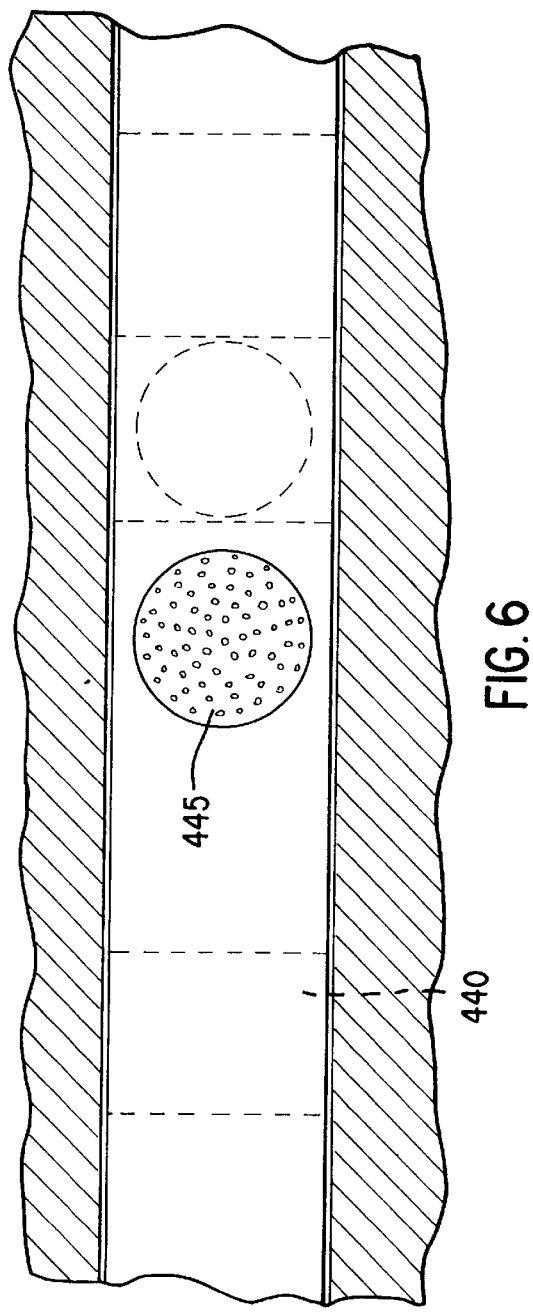

PRESSURIZED FEEDSHOE APPARATUS AND METHOD FOR PRECOMPACTING POWDERED MATERIALS

This is a Divisional of Ser. No. 08/705,343, filed Aug. 29, 1996, which in turn is a continuation-in-part of Provisional Patent Application No. 60/019,945, filed Jun. 14, 1996.

BACKGROUND OF THE INVENTION

1. Field of the Invention

This invention relates generally to feed shoes for feeding and depositing finely divided or particulate material into a die cavity for compacting. More particularly, the invention relates to a feed shoe that controls the delivery of particulate materials into the die cavity. This controlled delivery provides the particulate materials in the die cavity with a uniform density that is greater than what would otherwise be the bulk density of the particulate material or with a density gradient. The present invention also pertains to a process for precompacting particles in a die cavity to produce articles of uniform density or gradient density from particulate material.

2. Description of Related Art

In powder metallurgy and other technologies using particulate materials such as ceramics and carbides, products and parts are formed by pressing finely ground or atomized powders into a desired shape within a die cavity. Generally, the powders are compacted in the die cavity at room temperature and the then semi-dense compact is removed from the die and heated to bond the powders into a unified, dense mass. In powder metallurgy, the heat bonding procedure is generally known as sintering or in the case of ceramics and carbides, firing.

When these and similar procedures are employed, means are required for delivering measured amounts of powder or particulate to a die cavity on a powder press. Typically, feed shoes operate to deliver the powder or particulate material to the die cavity during the press cycle by using a gravity fill system. This system involves the movement of the feed shoe containing particulate material on a shuttle which slides the shoe forward along the table of the die press to a position at which the bottom feed hole of the feed shoe is exposed, overlies and registers with the die cavity furnishing enough loose powder to gravity fill the die cavity. Thereafter, the shuttle slides the shoe back along the table of the die press into a retracted position thereby cutting off the gravity flow of particulate material from the bottom hole of the feed shoe.

The particulate material is then pressed into an article and the article is ejected from the die. The shuttle then slides the shoe forward along the table of the die press displacing the ejected article and again exposing the bottom hole of the feed shoe as it overlies and registers with the die cavity thereby allowing gravity to fill the die cavity once again. The feed shoe is retracted once again thereby cutting off the gravity flow of particulate.

These known simple gravity feed methods deliver particles into die cavities at a density that is roughly equivalent to the bulk density (density of a bulk volume of the particles) of the particulate material. Because of gravity, all areas of the die cavity do not fill uniformly. Thus they do not provide for a uniform density of particulate material within the cavity. Articles produced by these feed methods are many times unsatisfactory because when pressed, they produce compacted parts that are also non-uniform in density. These non-uniformly dense articles are then prone to stress related cracking, especially upon ejection from the die cavity. These cracks are often only visible after sintering. Typically, with an almost spherical powder such as for example, copper coated aluminum powder, the fill ratio of amount of powder in die to size of compacted part is 3:1 using gravity to fill the die cavity. That is, the three dimensional size of the powder in the die is three times that of the final compacted article.

Shaking or vibrating a feed shoe is frequently employed in the art for inducing a more regular flow of the particulate material into the die cavity. This, however, is time consuming so and is generally not adequate to achieve uniform density of the particles in the die cavity or compacted articles of uniform density which are reproducible from article to article in a controlled manufacturing process.

Additionally, this shaking or vibrating of fine particles in known particle feed methods dislodges "fines" and dust from the particles which are then air borne to coat and contaminate the surrounding environs. Many of the particulate materials are frequently quite costly and in some cases toxic. Thus, the dust problem can represent a considerable economic loss or health hazard. Consequently, relatively elaborate and costly dust recovery systems and personnel safety precautions, such as filtered masks are presently used.

U.S. Pat. No. 4,813,818 to Sanzone discloses a feed shoe having a hopper for receiving powder materials from a source that communicates through a feeder tube with an enclosed filling chamber. The filling chamber is equipped with a vacuum. The vacuum is applied to assist the gravity flow of the powders through the feeder tube into the filling chamber. However, like the shaking or vibration techniques described above, such evacuation of the chamber does not provide for the uniform density of particulate material within a die cavity necessary to produce homogenous articles and materials that must exhibit uniform mechanical and physical properties. Examples of such articles or materials are those used in thermal management, etc. in which strict uniformity of properties (i.e., coefficient of thermal expansion, thermal conductivity, etc.) throughout the article or from article to article is required. Further, this chamber evacuation cannot be used to control the density of the particulate material in the die cavity and thereby create a density gradient of the particulate material and in the resultant compacted article.

Additionally, technologies exist for controlling and moving mechanical parts of die presses at much faster rates than those presently being employed. However, the rate at which die presses can produce articles is limited by the rate at which the die cavity can be filled with particulate materials. This rate is relatively slow using known feed shoes which use gravity to feed powders into the die cavity and does not allow the die presses to reach their maximum capacity for producing compacted parts and is even slower using vibratory methods.

Moreover, in the aforementioned and other known feed shoes, the step of retracting the feed shoe by dragging the feed shoe over the upper surface of the wear plate of the die table has been necessary to cut off the flow of particulate materials from the feed shoe. This retraction of the feed shoe after filling the die cavity, however results in the buildup of powders in the die near the trailing edge of the feed shoe. This friction induced "wedging" effect further exacerbates the problem of producing articles of non-uniform density upon compacting the particulate material in the die cavity, with all of the accompanying aforementioned disadvantages.

SUMMARY OF THE INVENTION

The present invention solves the aforementioned and other problems by providing a feed shoe that feeds particulate material into a die cavity at supra-atmospheric pressure to obtain a density that is uniform and greater than the bulk density of the particulate material. The fill ratio of a typical powder such as for example copper coated aluminum using the present invention pressurized feed shoe is reduced from 3:1 to about 2.3:1. The present invention feed shoe also allows the delivery of the particulate material to be controlled so that a density gradient is created within the particulate material in the die cavity. Compacted articles of graded density can thereby be produced.

The present invention also solves the problem of friction induced density irregularities (wedging) in the compacted articles by providing an apparatus that moves the feed shoe body forward in a horizontal plane that is above and transverse to the die cavity. The feed shoe body is moved to a position whereby the egress opening overhangs the die cavity. A device for downwardly moving the feed shoe body to register the egress opening with the die cavity is also provided.

The present invention further comprises a valve associated with the egress opening having a closed position for containing particulate material inside the feed shoe when the feed shoe body overhangs the table of the die press and an open position for delivering particulate material to the die cavity when the egress opening registers with the die cavity. This valve is "dripless", (i.e., it does not permit any particulate material from dripping out when it is in the closed position) and is so constructed to resist particle induced jamming or clogging. By providing this valve associated with the egress opening of the feed shoe, the feed shoe can be raised above the die cavity to prevent friction induced wedging in the particulate material.

The present invention also provides a process for controlling the delivery of particulate material to a die cavity for producing articles of uniform density or gradient density from particulate material(s) and of different types and different inherent densities. The process involves a pre-compaction step for delivering the particulate material to a die cavity to produce a uniform density of the particulate material therein. The particulate material in the die cavity to is then compacted to form an article having uniform density.

The present invention further provides a process for producing articles of a uniform density, which includes delivering particulate material to a die cavity, generating supra-atmospheric pressure within the die cavity, and compacting the particulate material to form an article having uniform density. A process for producing articles having a density gradient is also provided. In such a process, the powder delivery step is accomplished by varying the supra-atmospheric pressure within the die cavity.

BRIEF DESCRIPTION OF THE DRAWINGS

FIG. 4 is a top view of FIG. 1 in the fill position;

FIG. 5 is a side view of an egress valve on a feed shoe according to one embodiment of this invention; and FIG. 6 is a top view thereof schematically illustrating an open and a closed position of the valve.

DETAILED DESCRIPTION OF PREFERRED EMBODIMENTS

Figure 1:
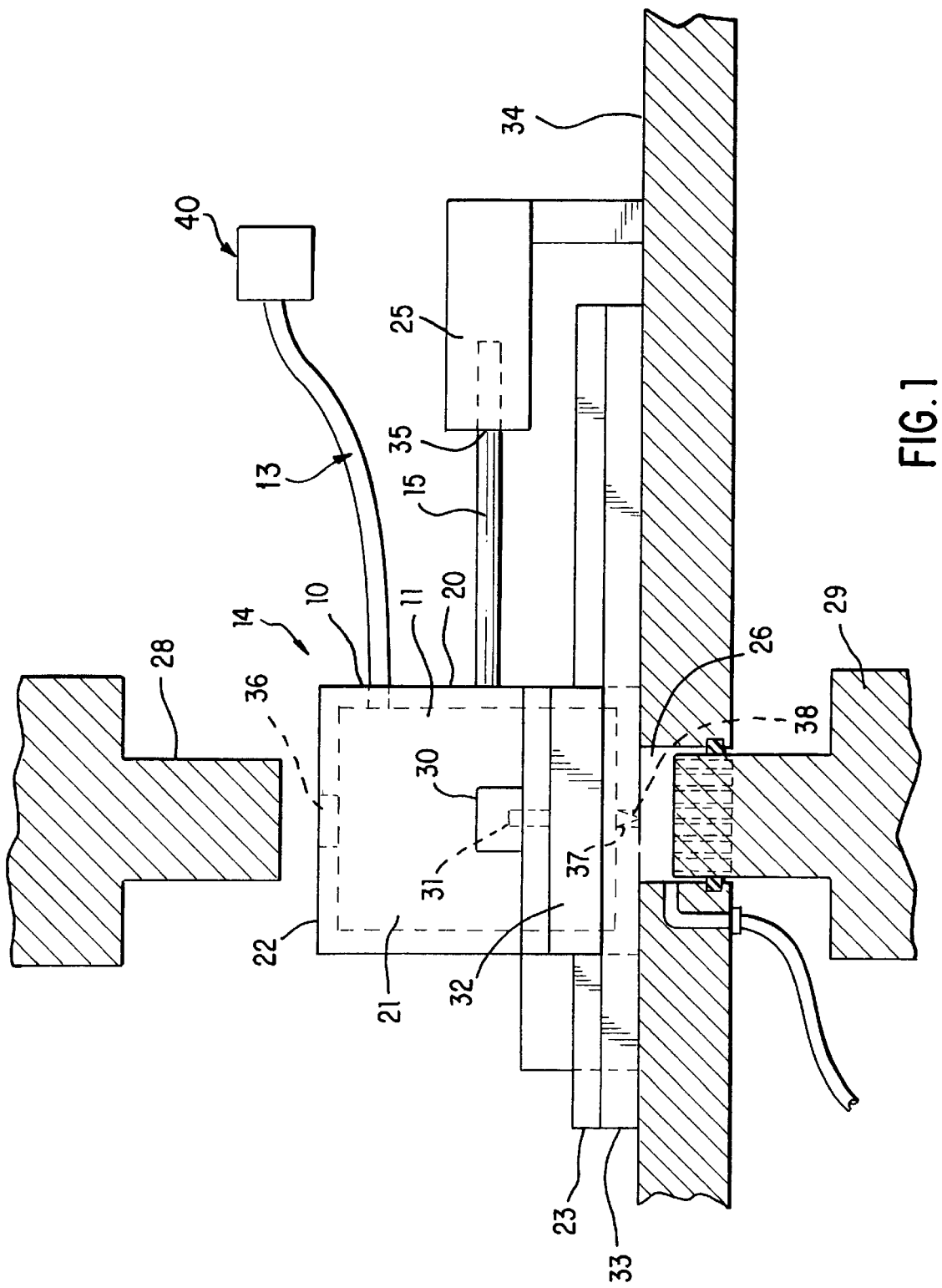
FIG. 1 is a side elevation of a feed shoe according to one embodiment of this invention.

Referring now to the embodiment illustrated in FIG. 1, the features of a preferred feed shoe 10 are shown. Feed shoe 10 as shown relates to the feeding and delivery of powdered metals into die cavity 26, the powdered metals being compacted by upper and lower punches 28 and 29. The teachings of this invention, however, are not limited to the handling of metal powders, but are equally applicable to the handling of particulate materials of various weights and types including, for example, ceramics, polymers, carbides, or cements (cementatious materials blended with water).

As shown in FIG. 1, pressurized feed shoe 10 generally comprises feed shoe vessel 11, and pressure conduit 13 communicating with vessel 11 through air ingress 14. A pressure generator 40 for generating supra-atmospheric pressures within vessel 11 and die cavity 26 for delivering powder material into die cavity 26 with a uniform density which is greater than the bulk density of the powder material communicates with vessel 11 via pressure conduit 13 sealingly engaged thereto. Alternatively, the pressure generator can be used to vary the density of the powder material in the die cavity along a gradient by varying the pressure generated during powder delivery. Feed shoe 10 is organized to cooperate with pneumatic piston 15 and actuator cylinder 25, or any other suitable mechanical linkage known to those in the art for selectively reciprocating the pressurized feed shoe such as cams, motors, gears, hydraulic pistons, stepping motors, linear motion transducers, servio motors, etc. as will appear more clearly in association with the operational description hereinafter. Delivery of the feed shoe 10 to and from the die cavity 26 can be in a linear or non-linear motion (i.e., swinging or pivoting back and forth) over the die cavity 26.

Shoe vessel 11 is preferably constructed of any material, such as a metal or metal alloy, that is suitable for withstanding supra-atmospheric pressures and includes rear wall 20 having a pair of laterally spaced side walls 21, 21A depending from a planar top wall 22 thereof. Powder ingress 36 is situated in planar top wall 22 and communicates with an optional hopper (not shown) receptive of a quantity of powder material. Powder ingress 36 is associated with an ingress valve (not shown) for maintaining pressure within shoe vessel 11 after and while it is pressurized. When present, the hopper has a discharge opening at the lower end thereof and communicates with the interior of vessel 11 through a filling conduit (not shown) which enters powder ingress 36. One each of a pair of bridge members 23 extend from the bottom exterior of side walls 21, 21A and have elevation cylinders 30 mounted thereon. Piston 31 is mounted at its bottom end to guide 32 and slidably engages the interior of elevation cylinder 30. In operation, pressure is applied to elevation cylinder 30 and the pressure forces the spatial separation of piston 31 from elevation cylinder 30 thereby elevating bridge member 23 to lift feed shoe vessel 11. Rail 33 is fixed to the wear plate of die table 34, and guides 32 slide freely in a self-aligning linear motion along rails 33, actuated by piston 15 sliding through opening 35 inside actuator cylinder 25 that is fixed to the wear plate of die table 34. In use, by applying a pressure to actuator cylinder 25 forcing the forward movement of piston 15 which is attached to feed shoe 10, feed shoe 10 moves forward. Actuator cylinder 25 can be operationally joined to any source of reciprocating motion, so that pressurized feed shoe 10 may be translated linearly in operation to and from a die cavity for the production of powdered metal products. For that purpose, opening 35 is provided in actuator cylinder 25 to accept piston 15.

Vessel 11 has bottom egress opening 37. Valve 38 is associated with egress opening 37 and has a closed position for containing powder material inside vessel 11 and an open position for delivering powder material to die cavity 26 when egress opening 37 registers with die cavity 26. In applications where it is necessary or desirable to deliver more than one type of particulate material to the die cavity, the feed shoe can have more than one egress opening 37 (not shown). Additionally, where it is desirable to deliver particulate material into very wide parts such as rings, gears etc., the feed shoe can have multiple egress openings (not shown).

Figure 2:
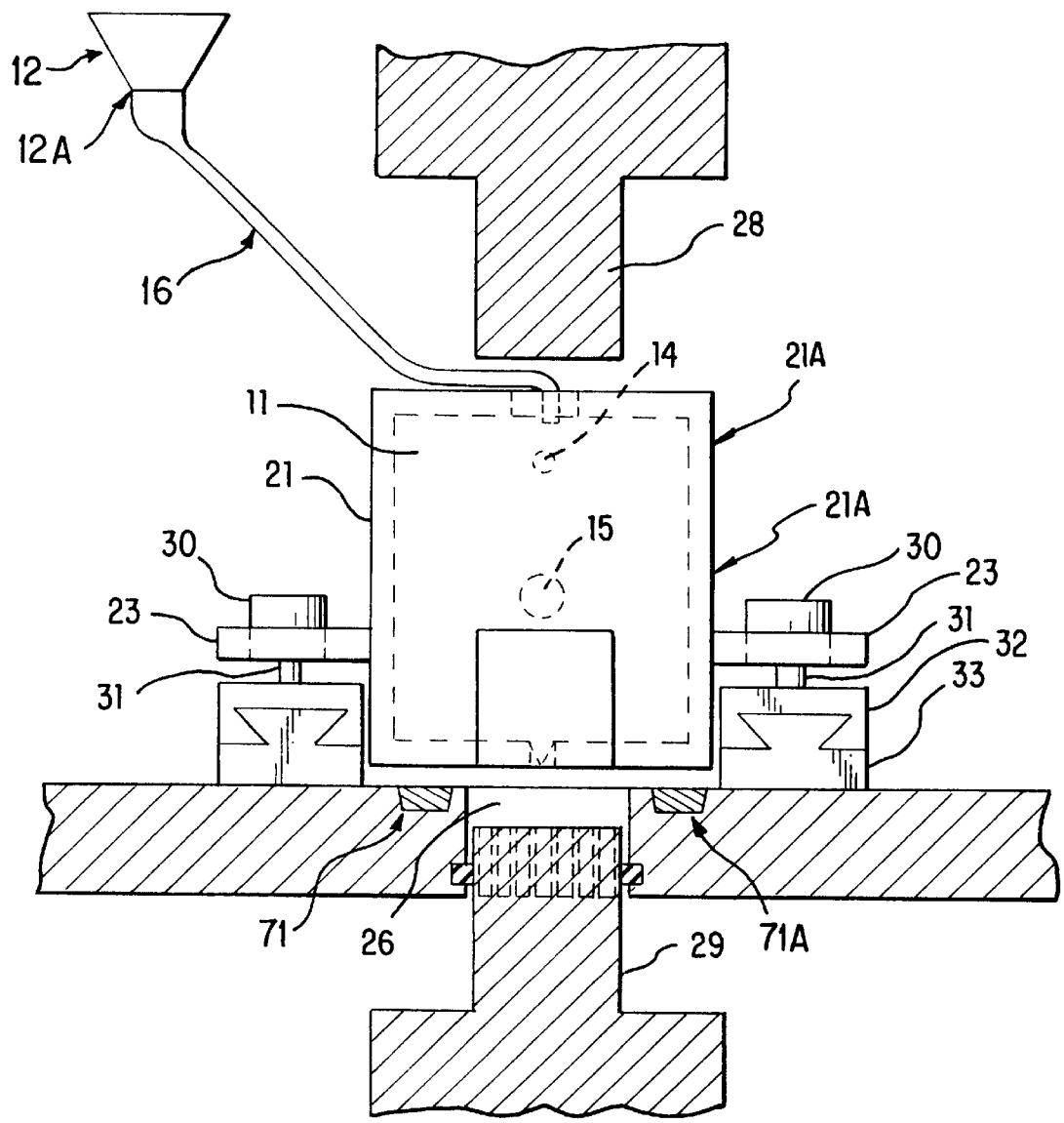
FIG. 2 is a front view of FIG. 1 showing the feed shoe in a horizontal plane elevated above and transverse to the die cavity.

FIG. 2 is a front view of FIG. 1 and shows the feed shoe 10 in an elevated position above and offset from the die cavity 26. In this position, powder material is prevented from entering the die cavity 26. As described with respect to FIG. 1, piston 31 is mounted to guide 32 and slidably engages the interior of elevation cylinder 30. The elevation cylinder 30 is attached to bridge member 23, which in turn is connected to the side walls 21, 21A of the feed shoe vessel 11. In FIG. 2, pressure has been applied to elevation cylinder 30 to force the separation of piston 31 from the elevation cylinder 30 in the upward direction indicated by the arrow. The upward movement of the elevation cylinder 30 in turn causes the bridge member 23 to lift in the same upward direction, thereby also raising the feed shoe vessel 11. The feed shoe 10 is thereby spatially separated from the die cavity 26.

Continuing with respect to FIG. 2, once the feed shoe 10 is in an elevated position, the feed shoe 10 moves transverse to the die cavity 26. This movement is accomplished by applying a pressure to actuator cylinder 25 (see FIG. 1) to force the movement of piston 15 through the opening 35 in the actuator cylinder 25. The movement of piston 15 causes guides 32 to slide along rails 33, so that the feed shoe 10 is moved to its final position above and transverse to the die cavity.

Figure 3:
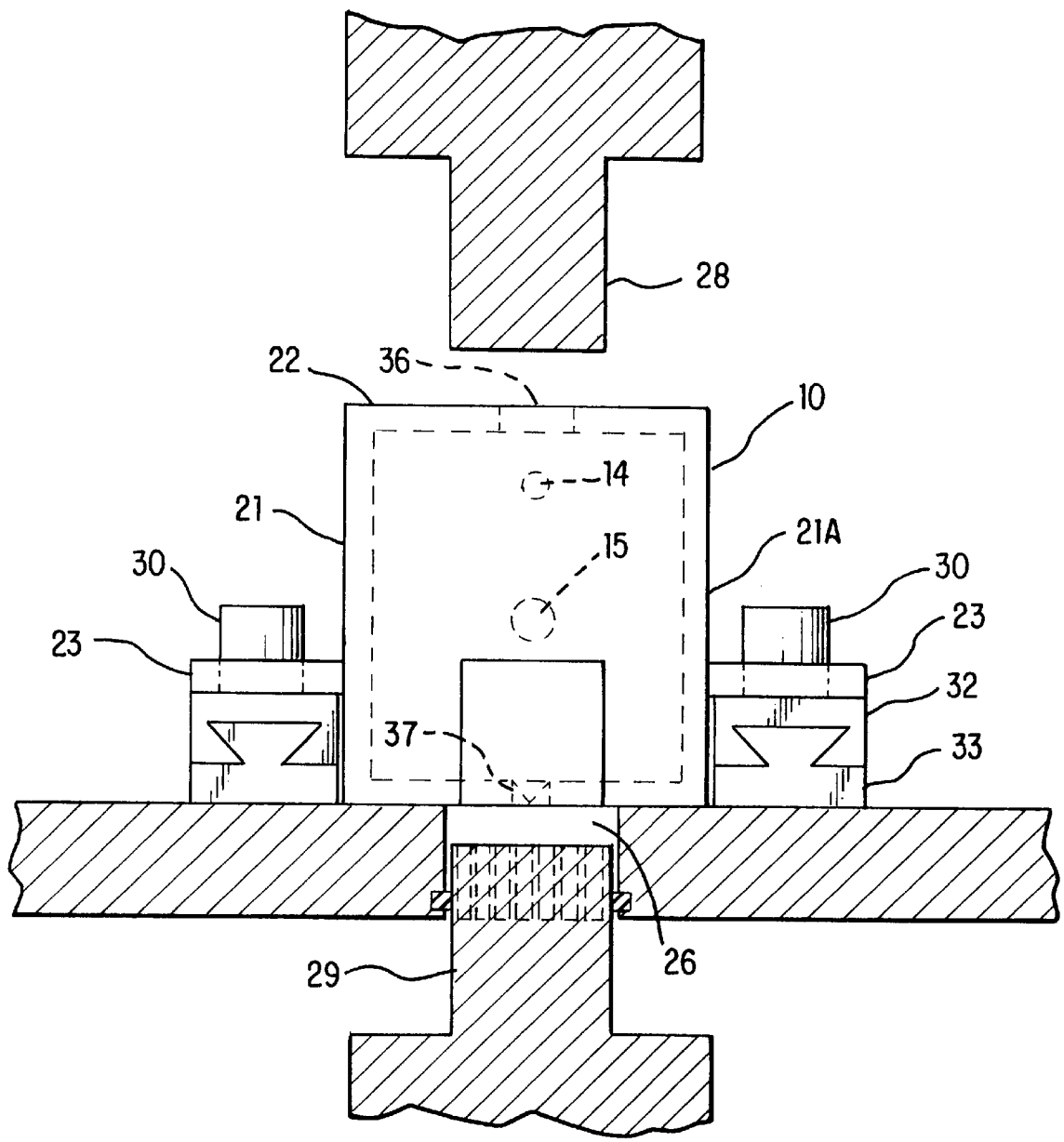
FIG. 3 is a front view of FIG. 1 showing the feed shoe in fill position.

When it is desired to fill the die cavity 26 with a powdered material, the movements described with respect to FIG. 2 are simply reversed. That is, an opposite pressure is applied to actuator cylinder 25, such that piston 15 moves back out of the actuator cylinder 25. The movement of piston 15 in the opposite direction causes guides 32 to slide back on rails 33 until the feed shoe 10 is positioned above the die cavity 26. An opposite pressure is then applied to lower elevation cylinder 30 and force piston 31 back into the elevation cylinder 30. Bridge member 23 is thereby lowered in accordance with the movement of elevation cylinder 30, and accordingly, feed shoe vessel 11 also lowers and is locked in the lowered position until after pressurization of feed vessel 11. The movement of feed shoe vessel 11 halts when egress opening 37 registers with die cavity 26. The feed shoe 10 is then in position to transfer powdered material to the die cavity 26. FIG. 3 shows the feed shoe 10 in the position for filling the die cavity 26. A lock 71, 71A or locking mechanism, as for example, a strong magnet, keeps the feed shoe registered with the die cavity during pressurized delivery of the particulate material therein.

Referring now to FIG. 5, the transfer of powder to the die cavity 426 is described in more detail. Valve body housing 438 is sandwiched between pressure vessel 411 and die cavity 426, defines valve cavity 439, and has upper body housing surface 440 and lower body housing surface 441. Upper body housing surface 440 has powder ingress 442 and lower body housing surface 441 has powder egress 443. Powder ingress 442 and powder egress 443 are aligned transverse with each other along a vertical axis. Valve slide 444 has slide hole 445 bored there through and sits within valve cavity 439. In operation, to open valve 437, air pressure (or an inert gas such as argon or helium) is provided through valve opening end 446 into valve cavity 439 to move valve slide 444 in a linear motion so as to align slide hole 445 with powder ingress 442 and powder egress 443 thereby creating open communication between vessel 411 and die cavity 426. To close valve 437, air pressure is applied through valve closing end 447 into valve cavity 439 to move valve slide 444 to a position whereby slide hole 445 is not aligned with powder ingress 442 and powder egress 443 thereby closing communication between vessel 411 and die cavity 426 cutting off powder flow. Lower body valve housing 441 has mechanical stops 446 and 447 for aligning and disaligning slide hole 445 with powder ingress 442 and powder egress 443.

FIG. 6 shows a top view of FIG. 5 viewed from within vessel 411 down through powder ingress 442, slide hole 445 which is aligned with powder ingress 442 and powder egress of valve body housing 438 in the open position. In the closed position, slide hole 445 is disaligned from powder egress 442 and powder ingress 443 so that there is no longer open communication between vessel 411 and die cavity 426.

In choosing the appropriate dimensions for slide 444 and valve body housing 438, consideration must be given to the size of the smallest powders used. The space between the slide 444 and the interior valve housing 438 should preferably be smaller than the smallest powder particle to minimize jamming of the valve mechanism by powder.

Figure 7:
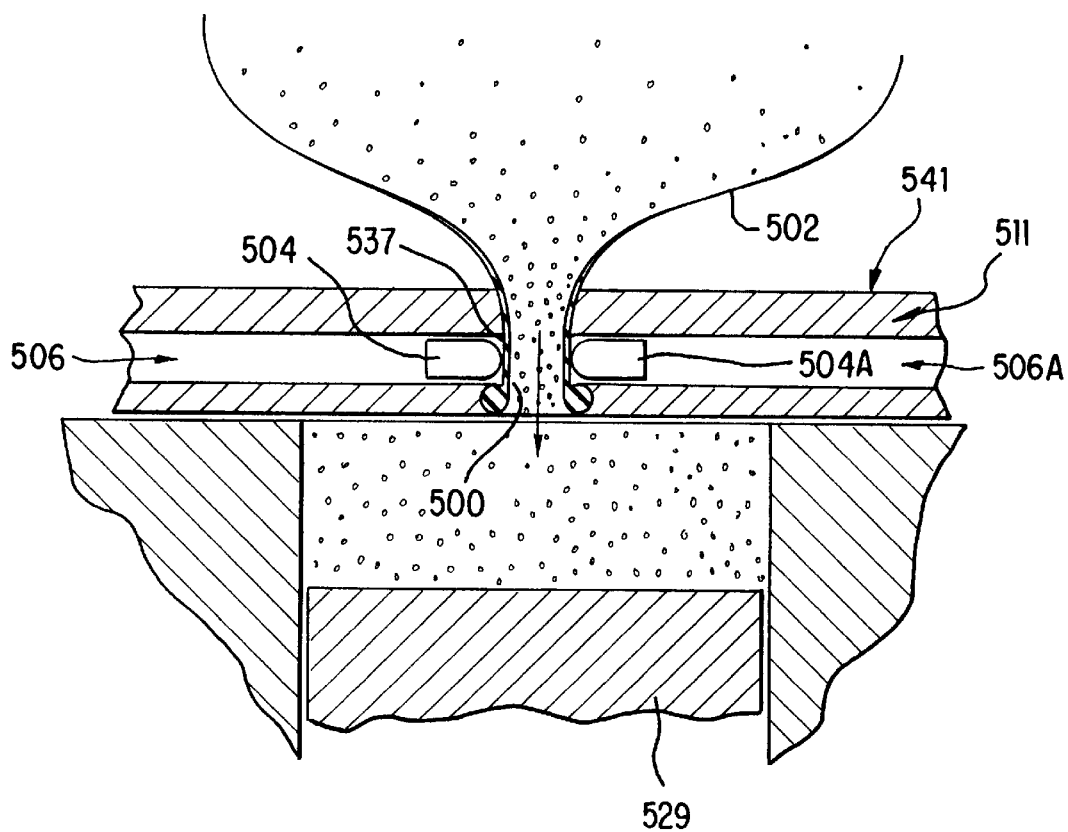
FIG. 7 is a front view of a pinch valve embodiment of an egress valve in the open position on the feed shoe.
Figure 8:
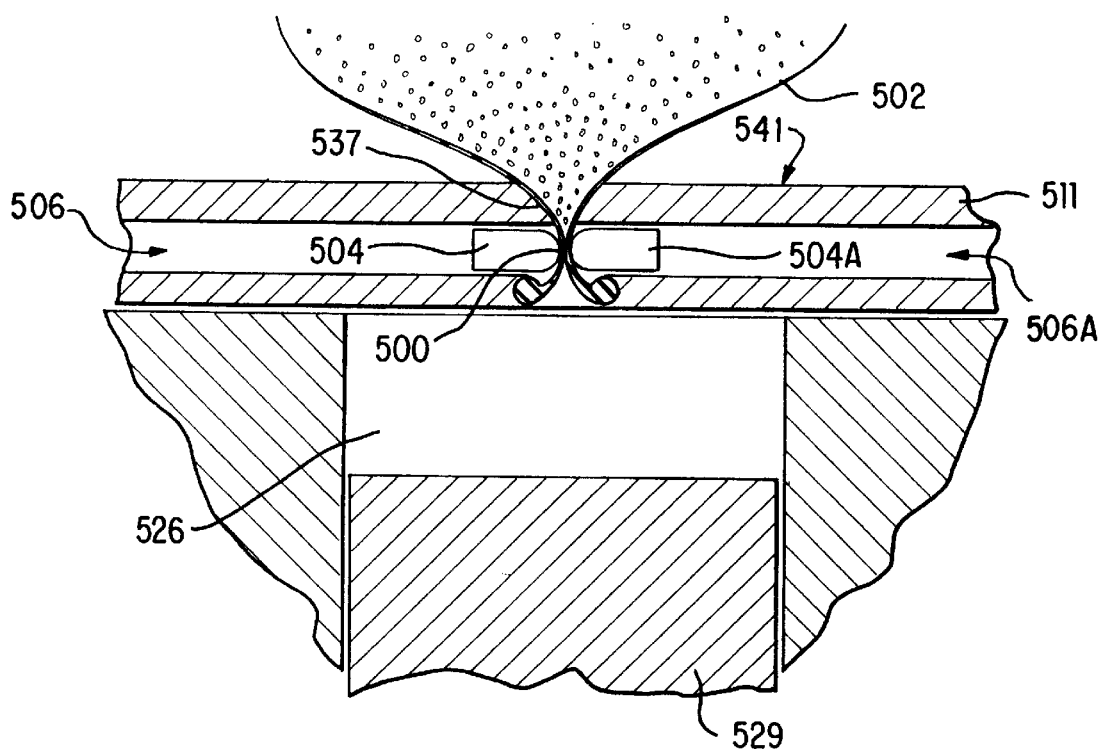
FIG. 8 is the pinch valve of FIG. 7 in the closed position.

Other methods or devices for cutting off the flow of powder from the feed shoe vessel to the die cavity may be utilized. For example, a valve in which powders are not in contact with mechanically moving parts can be used. In this embodiment, as illustrated in FIGS. 7 and 8, flexible feed tube 500 extends through bottom egress opening 537 and communicates with and is continuous with bladder 502 that lines the interior of feed shoe vessel 511. Flexible feed tube 500 is opened and closed by pinching and releasing the outside diameter of the tube. Mechanical pinchers 504, 504A are caused to pinch flexible feed tube 500 closed by the application of air through conduits 506, 506A in lower body housing 541 of feed shoe vessel 511. Alternatively, mechanical pinchers 504, 504A (as shown are pistons with rounded "pinching" ends) may begin in the pinched or closed position as shown in FIG. 8 and slide outward along conduits 506, 506A to open when pressure is generated within feed shoe vessel 511. Any suitable pinch valve apparatus may be employed as the egress valve. Preferably the pinch valve has the ability to "pinch off" immediately above the die surface of die cavity 526 sitting above lower punch 529.

Figure 9:
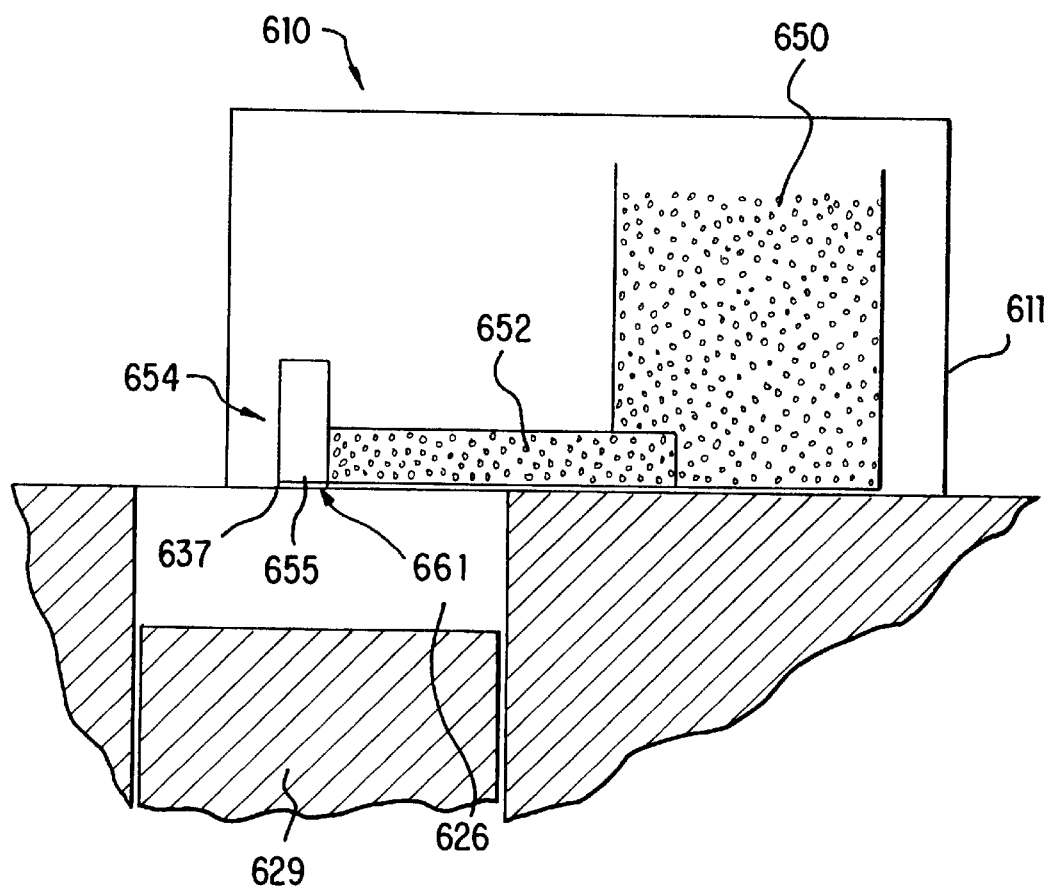
FIG. 9 is a side view of a pneumatic valve embodiment of the egress valve on the feed shoe.

FIG. 9 shows yet another embodiment of the bottom egress valve 637. In detail, hopper 650 sits within vessel 611 and is receptive of a quantity of particulate material. Feed tube 652 communicates between the interior of hopper 650 and egress vacuum tube 654, the bottom opening 655 of which registers with bottom egress opening 661 of feed shoe vessel 611 and with die cavity 626 above lower punch 629 when feed shoe 610 is in the fill position. In use, supra-atmospheric pressure is delivered through egress vacuum tube 654 which serves to pull particulate material from hopper 650 through feed tube 652 into egress vacuum tube 654 and finally into die cavity 626 through egress opening 661. When the supra-atmospheric pressure is shut off, the flow of the particulate material into die cavity 626 is cut off. The supra-atmospheric pressure also serves to precompact the particulate material in the die cavity.

FIG. 4 shows an embodiment of the present invention comprising elevation cylinder 330,330A, guides 332,332A, piston 315, actuator cylinder 325, upper punch 328, piston 331, powder ingress 336, bottom egress opening 337, and further comprising a second conduit 348 extending between and openly communicating between a source of liquid solutions (not shown) and the interior of die cavity 326 when feed shoe 310 is in fill position. Second conduit 348 delivers liquid solutions to said die cavity. Alternatively, second conduit 348 can deliver the liquid solution to the interior of feed shoe vessel 311. Second conduit 348 can be constructed from a solenoid valve, as for example a zero dead volume solenoid valve, however, any dripless valve may be used. Solenoid valve housing 345 encases second conduit 348. A vacuum may be attached to the second conduit 348 to remove the liquid from the die cavity after it has been dispensed therein. Such a second conduit is appropriately used in those situations wherein it is preferable to add a liquid component to the die cavity prior to compacting the particles. Such liquid components can include, but are not limited to, aqueous solutions, lubricants, surfactants or activation solutions for atomically cleaning metal particulates for cold welding. The liquid components can also include any solution which is desired to be incorporated into the material, for example, water added to cement or plaster, hardener added to a polymer, solvent added to a polymer, etc. Feed shoes according to the present invention using activation solutions for atomically cleaning the particulate materials are useful in producing net or near net shaped parts without the need for sintering. In embodiments where the vacuum is attached to the second conduit for removing liquid solutions from the die cavity (or alternatively the feed shoe vessel), it is useful to have a selective barrier 372 situated inside the second conduit at a point between the source of liquid solutions and the interior of the feed shoe. When the vacuum is applied to the second conduit, the selective barrier prevents particulate material from being removed with the liquid.

As an alternative to removing liquid solutions from the die through the second conduit 348, a vacuum may be applied to the die cavity or to the lower punch or both. In use, liquid solution is sprayed into the die cavity through the second conduit and then removed from of the die cavity by the vacuum attached thereto. The second conduit can alternatively deliver liquid components to the interior of the feed shoe vessel. In those instances where a liquid solution is used to atomically clean metal powders for cold welding and the liquid is delivered to the interior of the feed shoe vessel as opposed to the die cavity, a vacuum or other liquid removing means is applied to the feed shoe vessel to remove the liquid component before the powders are delivered to the die cavity. In this embodiment, the present invention also further comprises any known device for providing an atmosphere of an inert gas, as for example helium or argon, a gas such as nitrogen or an active gas such as $O_2$, $O_3$, and $SO_2$ around the atomically cleaned metal powders until they can be compressed in the die cavity.

The present invention also provides a process for producing articles of uniform density from particulate material. The process comprises the steps of delivering particulate material to a die cavity, generating a supra-atmospheric pressure within the die cavity to produce a uniform density of the particulate material that is greater than the material's bulk density or generating a gradient of pressure used to deliver the particulate material to the die cavity with a gradient of densities, and compacting the particulate material to form an article having a uniform density. Additional steps may be utilized if it is desired or necessary to add liquid components to the particulate material. The process can further comprise repeating the pressurized delivery step with a second or third particulate material.

Figure 10:
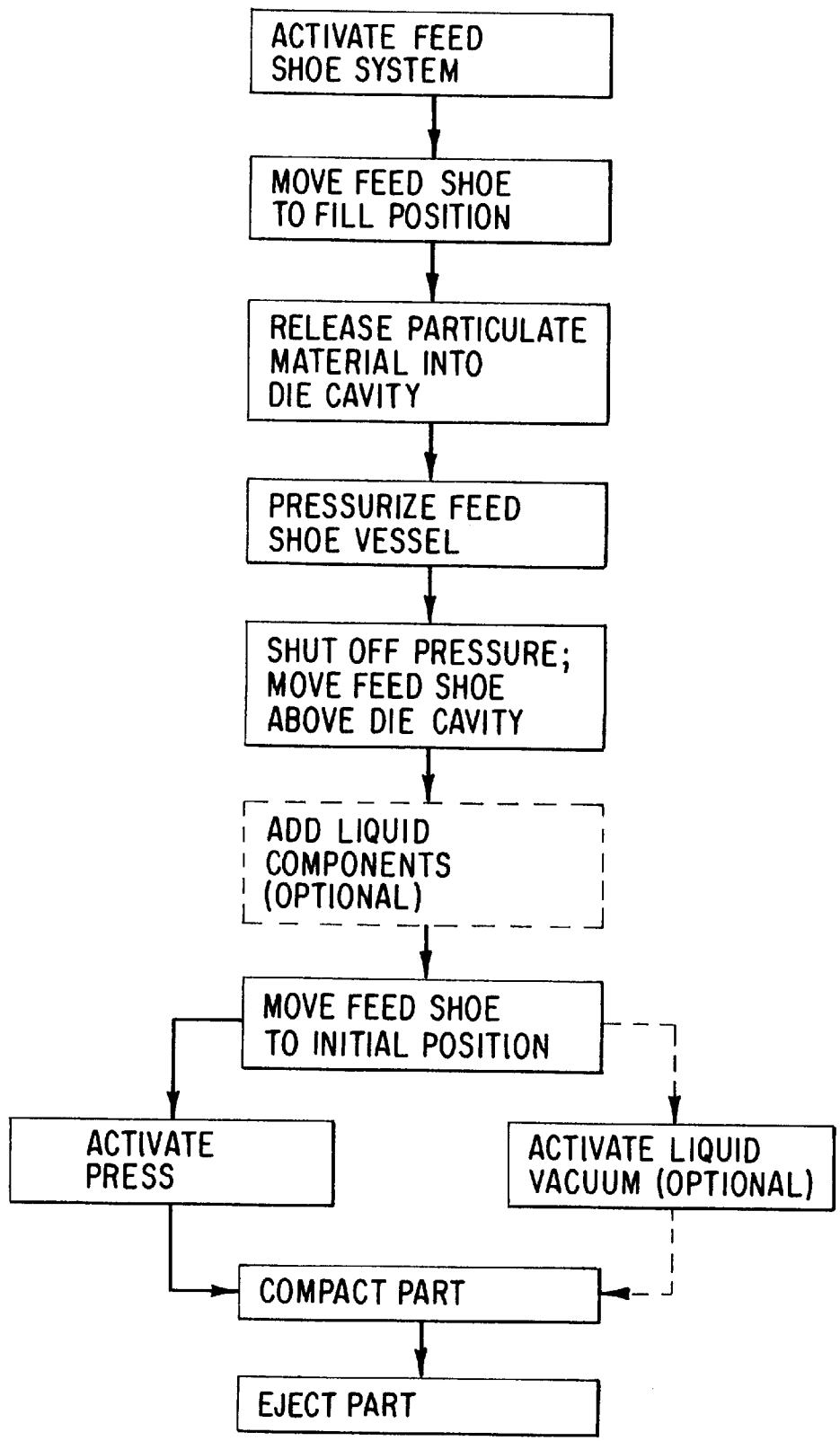
FIG. 10 is a diagram of a flow chart illustrating a process of the present invention.

One embodiment of the inventive process is depicted in flow chart form in FIG. 10. At a specified time in the part making cycle, a controller (which may be computer-driven) activates the feed shoe system. The controller instructs the feed shoe system to (1) move the feed shoe out over the die cavity, and (2) lower the feed shoe to register with the die cavity to a fill position. The description for FIGS. 1–3 provides sufficient detail on how such movement may be accomplished. (3) Particulate material is then released from the hopper; (4) powder ingress valve opens; (5) particulate material is fed through powder ingress of the feed shoe into the feed shoe vessel, the powder ingress valve closes; (6) powder egress valve opens; (7) particulate material flows into the die cavity through the egress valve. (8) As the particulate material is released, the feed shoe vessel is pressurized at a specified pressure for a specified time or at varying pressures for varying times. As an example only, if copper coated aluminum is the particulate material, the feed shoe vessel should be pressurized to about 25 pounds for 1 seconds. Suitable pressures for use with the present invention, however, are readily optimizable and may range from about 1 to about 125 pounds or higher and generally vary depending on the size of the die cavity, the complexity of the geometry of the die cavity, and the degree of difficulty in uniformly filling the die cavity. Suitable times for pressurizing are also readily optimizable and may range from less than 1 second to minutes or longer. The applicable time is also based on the size and complexity of the geometry of the die cavity and the degree of difficulty in uniformly filling the cavity.

Alternatively, particulate material that has been pre-delivered to the feed shoe vessel is delivered to the die cavity with the simultaneous application of pressure and opening of the egress valve. In either case the die cavity is then filled with particulate material. In certain applications, it may be useful to fill the cavity in more than one place to accommodate a unique or complex part geometry.

In the next step of the process, after the pressure in the feed shoe vessel is shut off and the egress valve closes, the feed shoe is lifted above the die cavity. If it is necessary or advantageous to add liquid components to the particulate material, they may be added to the die cavity at this point in the process. The feed shoe is returned to its initial position, and a press is activated. At the same time, a vacuum may be activated if it is desired to remove liquid components that were added to the particulate material. A press punch is then lowered into the die cavity and raised up to the die cavity to compact the particulate material into the desired part. The press punch may displace any liquid component that may be present in the die cavity out of the part, such that the optional vacuum may remove the liquid component from the die cavity, if desired. Finally, a lower punch ejects the finished part from the die cavity.

Feed shoes according to the present invention can be adapted for use in any known powder press manufacturing process and can also be temperature-controlled as appropriate by, for example, insulation, heating with convection or induction, microwave systems or heat transfer methods that pump oil or hot water through pipes or coils.

In a further embodiment, the present invention is directed to a powder press for making parts from particulate materials. The powder press according to the present material comprises a feed shoe for delivering particulate materials to a die cavity and a wear plate defining a die table of the powder press. The feed shoe comprises a vessel for receiving a particulate material; a pressure generator for generating supra-atmospheric pressures in the die cavity and the vessel; and a shuttle for moving the feed shoe to a position whereby an opening in the feed shoe aligns with the die cavity. The shuttle is mounted on its underside to the upper surface of the wear plate. Particulate material is transferred to the die cavity through the feed shoe.

The present invention may be embodied in other specific forms without departing from the spirit or essential characteristics thereof. The present embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A process for precompacting particulate material in a die cavity, said process comprising the steps of:

(1) delivering said particulate material to a die cavity;
   (2) generating supra-atmospheric pressure within said die cavity to precompact the particulate material within said die cavity to a density that is greater than the bulk density of that particulate material; and
   (3) compacting said particulate material to form an article.

2. A process for precompacting particulate material in a die cavity, comprising the steps of:

(1) delivering said particulate material to a die cavity;
   (2) generating supra-atmospheric pressure within said die cavity to precompact the particulate material within said die cavity to a density that is greater than the bulk density of that particulate material;
   (3) compacting said particulate material to form an article; and
   (4) repeating the delivery step with at least one additional particulate material and the pressure step before carrying out the compacting step.

3. A process for precompacting particulate material in a die cavity, comprising the steps of:

(1) delivering said particulate material to a die cavity;
   (2) generating supra-atmospheric pressure within said die cavity to precompact the particulate material within said die cavity to a density that is greater than the bulk density of that particulate material; and
   (3) compacting said particulate material to form an article; wherein the supra-atmospheric pressure is varied during the pressure generating step, thereby creating a density gradient in the particulate material in the die cavity.

4. A process for precompacting particulate material in a die cavity, comprising the steps of:

(1) delivering said particulate material to a die cavity;
   (2) generating supra-atmospheric pressure within said die cavity to precompact the particulate material within said die cavity to a density that is greater than the bulk density of that particulate material;
   (3) compacting said particulate material to form an article; and
   (4) adding liquid solution to said particulate material prior to said compacting step.

5. The process of claim 4, further comprising the step of vacuuming out said liquid components before or during said compacting step.

* * * * *